United States Patent
Shimamura et al.

(10) Patent No.: US 10,745,518 B2
(45) Date of Patent: Aug. 18, 2020

(54) BRANCHING-TYPE POLYOXYETHYLENE COMPOUND AND CONTACT LENS

(71) Applicant: NOF CORPORATION, Tokyo (JP)

(72) Inventors: Yoshihisa Shimamura, Kawasaki (JP); Yosuke Matsuoka, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 111 days.

(21) Appl. No.: 16/096,738

(22) PCT Filed: Apr. 27, 2017

(86) PCT No.: PCT/JP2017/016705
§ 371 (c)(1),
(2) Date: Oct. 26, 2018

(87) PCT Pub. No.: WO2017/188372
PCT Pub. Date: Nov. 2, 2017

(65) Prior Publication Data
US 2019/0106539 A1 Apr. 11, 2019

(30) Foreign Application Priority Data
Apr. 28, 2016 (JP) ................ 2016-092129

(51) Int. Cl.
| | |
|---|---|
| C08F 299/02 | (2006.01) |
| C08G 65/02 | (2006.01) |
| C08G 65/332 | (2006.01) |
| C08F 116/12 | (2006.01) |
| C08L 71/02 | (2006.01) |
| G02B 1/04 | (2006.01) |
| G02C 7/04 | (2006.01) |

(52) U.S. Cl.
CPC ............ *C08G 65/02* (2013.01); *C08F 116/12* (2013.01); *C08F 299/02* (2013.01); *C08F 299/024* (2013.01); *C08G 65/3322* (2013.01); *C08L 71/02* (2013.01); *G02B 1/043* (2013.01); *C08G 2261/32* (2013.01); *C08L 2205/05* (2013.01); *G02C 7/049* (2013.01)

(58) Field of Classification Search
CPC ... C08H 1/00; C08H 1/02; C08H 1/06; C08H 3/00; C08H 6/00; C08H 8/00; C08H 99/00; C08G 65/02; C08G 65/3322; C08F 116/12; C08F 299/02; C08F 299/024; C08L 2205/05; C02G 7/049
USPC .......... 528/86, 125–175, 220–270, 373–425; 351/159.02
See application file for complete search history.

(56) References Cited

U.S. PATENT DOCUMENTS

2012/0245248 A1* 9/2012 Alli ................. C08F 290/068
523/107

* cited by examiner

*Primary Examiner* — Travis S Fissel
(74) *Attorney, Agent, or Firm* — Sughrue Mion, PLLC

(57) ABSTRACT

Provided is a silicone contact lens having surface hydrophilicity and surface lubricity. The silicone contact lens includes, on its surface, a graft polymer chain derived from a branched polyoxyethylene compound represented by the formula (1):

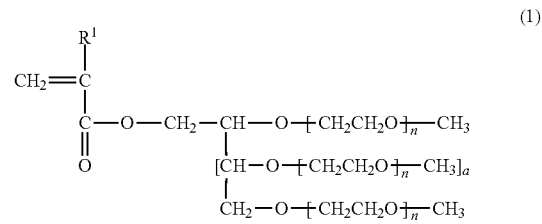

where n represents from 3 to 1,150, a represents 0 or 2, and $R^1$ represents a hydrogen atom or a methyl group.

6 Claims, No Drawings

BRANCHING-TYPE POLYOXYETHYLENE COMPOUND AND CONTACT LENS

TECHNICAL FIELD

The present invention relates to a branched polyoxyethylene compound and a contact lens.

The present application claims priority from Japanese Patent Application No. 2016-092129, which is incorporated herein by reference.

BACKGROUND ART

A silicone hydrogel contact lens has been known as one kind of contact lens. The silicone hydrogel contact lens has been expected to suppress eye diseases resulting from the oxygen deficiency of a cornea, such as an infectious disease, corneal vascularization, and corneal endothelial cell damage, because the lens has oxygen permeability drastically higher than that of a related-art contact lens. Meanwhile, silicone is a material having extremely strong hydrophobicity, and hence has involved a problem in that when the silicone is used as it is as a contact lens, corneal damage due to a tear breakup or friction with an ocular tissue in association therewith occurs. In view of the foregoing, companies developing silicone hydrogel lenses have been modifying the surfaces of the lenses through various methods to transform their physical properties into those applicable to eyes.

As a method of modifying the surface of a contact lens, a method involving using graft polymerization has already been known in the art. In Patent Literature 1, there is a description of a method involving subjecting the surface of a polysiloxane contact lens to graft polymerization with N,N-dimethylacrylamide to improve the hydrophilicity of the surface of the contact lens while maintaining its oxygen permeability.

In Patent Literature 2, there is a description of a method involving subjecting the surface of a base material, such as a polysiloxane, to graft polymerization with methacrylic acid, sodium methacrylate, sodium vinyl sulfonate, or sodium styrene sulfonate to improve the hydrophilicity of the surface of the base material.

In Patent Literature 3, there is a description of a method involving subjecting a silicone hydrogel base material to graft polymerization with a special zwitterionic group-containing monomer to improve the hydrophilicity and lubricity of the surface of the base material.

In Patent Literature 4, there are descriptions of a method involving mixing a water-soluble polymer, which is obtained by polymerizing a polyoxyethylene compound having a free radical-polymerizable group and having a weight-average molecular weight of from about 300 to about 500, into the package preservation solution of a hydrogel lens in advance, and treating the mixture with an autoclave to cause the polymer to physically adhere to the surface of the lens, and a method involving dissolving the water-soluble polymer in a monomer mixture in advance, and polymerizing the monomer mixture to provide a lens, thereby modifying the surface of the lens.

However, a method involving improving the hydrophilicity of the surface of a silicone hydrogel lens with a polyoxyethylene derivative having a branched chain length has not been known yet.

CITATION LIST

Patent Literature

[PTL 1] JP 02-228309 A
[PTL 2] JP 09-506665 A
[PTL 3] JP 2011-81394 A
[PTL 4] JP 2008-520668 A

SUMMARY OF INVENTION

Technical Problem

That is, an object of the present invention is to provide a silicone contact lens having surface hydrophilicity and surface lubricity.

Solution to Problem

The inventors of the present invention have made extensive investigations with a view to achieving the object, and as a result, have confirmed that a silicone contact lens including, on its surface, a graft polymer chain derived from a branched polyoxyethylene compound (hereinafter sometimes referred to as "monomer of the present invention") has surface hydrophilicity and surface lubricity. Thus, the inventors have completed the present invention.

That is, the present invention is as described below.

[1] A branched polyoxyethylene compound, which is represented by the following formula (1):

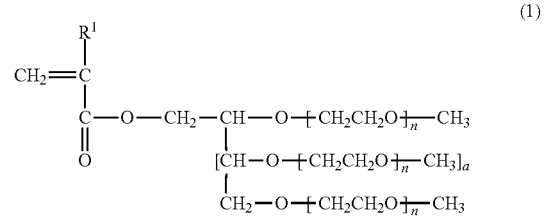

where n represents from 3 to 1,150, a represents 0 or 2, and $R^1$ represents a hydrogen atom or a methyl group.

[2] A silicone contact lens, including, on a surface thereof, a graft polymer containing a constituent unit represented by the following formula (1'):

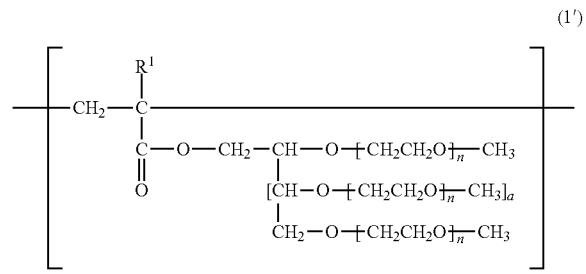

where n represents from 3 to 1,150, a represents 0 or 2, and $R^1$ represents a hydrogen atom or a methyl group.

[3] A contact lens, including a constituent unit represented by the following formula (1'):

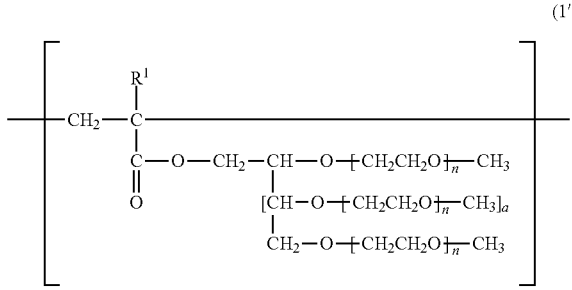

where n represents from 3 to 1,150, a represents 0 or 2, and $R^1$ represents a hydrogen atom or a methyl group.

[4] A branched polyoxyethylene compound according to the above-mentioned item 1, wherein the n represents from 3 to 600, the a represents 0 or 2, and the $R^1$ represents a hydrogen atom or a methyl group.

[5] A silicone contact lens according to the above-mentioned item 2, wherein the n represents from 3 to 600, the a represents 0 or 2, and the $R^1$ represents a hydrogen atom or a methyl group.

[6] A contact lens according to the above-mentioned item 3, wherein the n represents from 3 to 600, the a represents 0 or 2, and the $R^1$ represents a hydrogen atom or a methyl group.

[7] A method of producing a silicone contact lens including, on a surface thereof, a graft polymer containing a constituent unit represented by the following formula (1'):

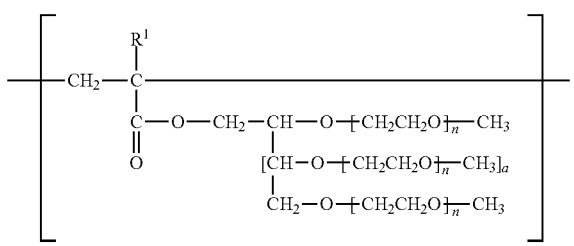

where n represents from 3 to 1,150, a represents 0 or 2, and $R^1$ represents a hydrogen atom or a methyl group.

[8] A method of producing a contact lens including a constituent unit represented by the following formula (1'):

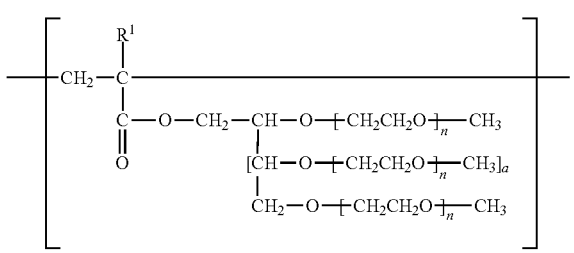

where n represents from 3 to 1,150, a represents 0 or 2, and $R^1$ represents a hydrogen atom or a methyl group.

[9] A surface treatment agent for a contact lens, including a branched polyoxyethylene compound represented by the following formula (1):

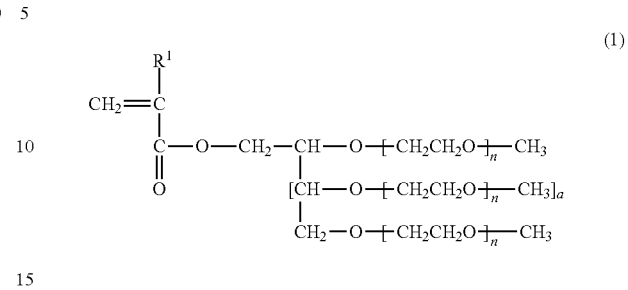

where n represents from 3 to 1,150, a represents 0 or 2, and $R^1$ represents a hydrogen atom or a methyl group.

[10] A surface treatment method for a contact lens, including using a branched polyoxyethylene compound represented by the following formula (1):

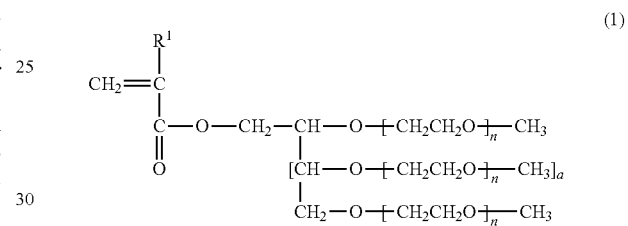

where n represents from 3 to 1,150, a represents 0 or 2, and $R^1$ represents a hydrogen atom or a methyl group.

[11] A branched polyoxyethylene compound for a surface treatment of a contact lens, which is represented by the following formula (1):

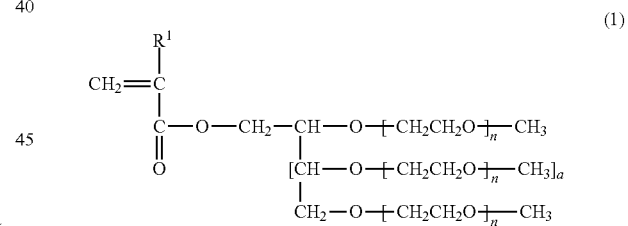

where n represents from 3 to 1,150, a represents 0 or 2, and $R^1$ represents a hydrogen atom or a methyl group.

[12] A use of a branched polyoxyethylene compound represented by the following formula (1) as production of a surface treatment agent for a contact lens:

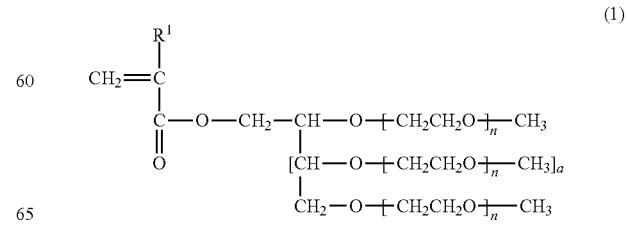

where n represents from 3 to 1,150, a represents 0 or 2, and $R^1$ represents a hydrogen atom or a methyl group.

Advantageous Effects of Invention

The silicone contact lens of the present invention has surface hydrophilicity and surface lubricity.

DESCRIPTION OF EMBODIMENTS

The present invention is described in more detail below.
[Monomer of the Present Invention]

A monomer of the present invention includes a branched polyoxyethylene in a molecule thereof, and is represented by the following formula (1).

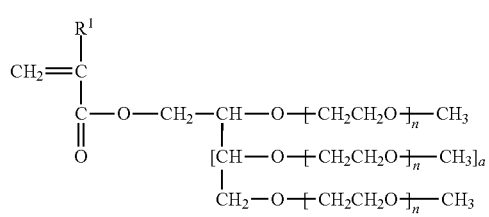

(1)

In the formula (1), n represents from 3 to 1,150, a represents 0 or 2, and $R^1$ represents a hydrogen atom or a methyl group. When the n represents 2 or less, sufficient hydrophilicity and sufficient lubricity cannot be imparted to the surface of a contact lens. When the n represents 1,151 or more, the viscosity of the monomer increases to make it difficult to uniformly treat the surface of the contact lens with the monomer, and hence a function of the contact lens is inhibited. The n is not particularly limited as long as the n falls within the range of from 3 to 1,150, and for example, the n may represent from 25 to 800, from 50 to 800, or from 50 to 600, or may represent from 5 to 45, from 15 to 25, from 200 to 250, from 220 to 230, from 425 to 475, from 447 to 457, or from 20 to 452. The n more preferably represents from 3 to 800, and most preferably represents from 3 to 600.

[Method of Synthesizing Monomer of the Present Invention]

Although a method of synthesizing the monomer of the present invention is not particularly limited, the following method may be given as an example thereof.

The monomer of the present invention can be obtained by esterifying, for example, a polyoxyethylene derivative A, B, C, or D described below through a known method.

Specifically, a polyoxyethylene derivative is dissolved in an organic solvent (e.g., toluene), and the solution is dehydrated. For example, triethylamine and acryloyl chloride {the monomer of the present invention to be finally obtained is such that the $R^1$ in the formula (1) represents a hydrogen atom} or methacryloyl chloride {the monomer of the present invention to be finally obtained is such that the $R^1$ in the formula (1) represents a methyl group} are added to the residue, and the mixture is subjected to a reaction for several hours.

Next, triethylamine hydrochloride in the organic solvent is removed, and impurities are removed by extraction or the like, followed by desolvation or the like. Thus, the monomer of the present invention can be obtained.

(Polyoxyethylene Derivative A)
The polyoxyethylene derivative A may be synthesized by a method described in JP 2004-197077 A, and is represented by the following formula (2).

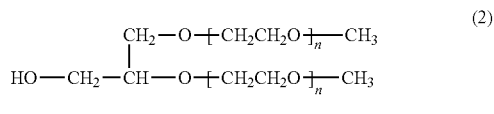

(2)

n = 225

(Polyoxyethylene Derivative B)
The polyoxyethylene derivative B may be synthesized by a method described in JP 2004-197077 A, and is represented by the following formula (5).

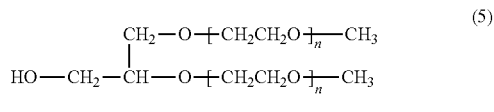

(5)

n = 452

(Polyoxyethylene Derivative C)
The polyoxyethylene derivative C may be synthesized by a method described in JP 2010-254986 A, and is represented by the following formula (7).

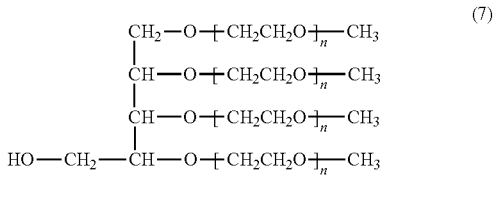

(7)

n = 225

(Polyoxyethylene Derivative D)
The polyoxyethylene derivative D may be synthesized by a method described in JP 2004-197077 A, and is represented by the following formula (10).

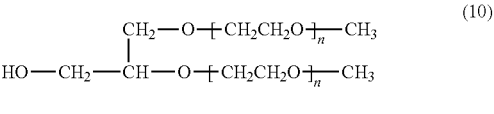

(10)

n = 20

[Silicone Contact Lens Including, on its Surface, Graft Polymer Containing Constituent Unit Based on Monomer of the Present Invention]

A silicone contact lens including, on its surface, a graft polymer containing a constituent unit based on the monomer of the present invention (derived from the monomer of the present invention) includes, on the surface, a graft polymer chain containing a constituent unit represented by the following formula (1'). In more detail, the surface of the silicone contact lens including, on the surface, the graft polymer containing a constituent unit based on the monomer of the present invention is chemically modified with the graft polymer chain containing a constituent unit that is derived from the monomer represented by the following formula (1) and is represented by the following formula (1').

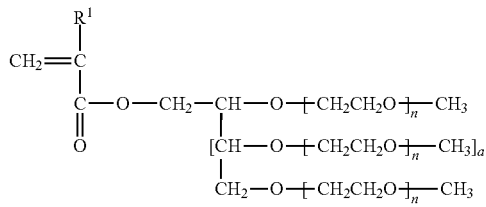

In the formula (1), n represents from 3 to 1,150, a represents 0 or 2, and $R^1$ represents a hydrogen atom or a methyl group.

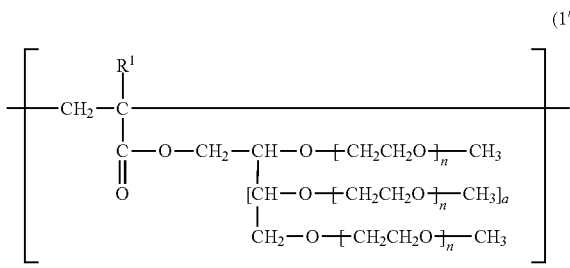

In the formula (1'), n represents from 3 to 1,150, a represents 0 or 2, and $R^1$ represents a hydrogen atom or a methyl group. When the n represents 2 or less, sufficient hydrophilicity and sufficient lubricity cannot be imparted to the surface of a contact lens. When the n represents 1,151 or more, the viscosity of the monomer increases to make it difficult to uniformly treat the surface of the contact lens with the monomer, and hence a function of the contact lens is inhibited. The n is not particularly limited as long as the n falls within the range of from 3 to 1,150, and for example, the n may represent from 25 to 800, from 50 to 800, or from 50 to 600, or may represent from 5 to 45, from 15 to 25, from 200 to 250, from 220 to 230, from 425 to 475, from 447 to 457, or from 20 to 452. The n more preferably represents from 3 to 800, and most preferably represents from 3 to 600.

When Surface Treatment Object is Silicone Hydrogel

Although the following materials may be given as examples of a silicone monomer to be used for a silicone hydrogel contact lens base material including, on its surface, the graft polymer containing a constituent unit based on the monomer of the present invention, 3-[tris(trimethylsiloxy) silyl]propyl methacryloyloxyethyl succinate (see WO 2010/082659 A1) is preferred.

Examples of (meth)acrylates each having a polydimethylsiloxane skeleton include α-methyl-ω-methacryloyloxypropyl polydimethylsiloxane (weight-average molecular weight: 1,000) and α,ω-dimethacryloyloxypropylpolydimethylsiloxane (weight-average molecular weight: 1,000). For example, FM-0711 or FM-7711 sold from JNC Corporation may be used.

Examples of (meth)acrylates each having a trimethylsiloxy group include 3-[tris(trimethylsiloxy)silyl]propyl (meth)acrylate (TRIS), 3-[bis(trimethylsiloxy)methylsilyl] propyl (meth)acrylate, and 3-[(trimethylsiloxy)dimethylsilyl]propyl (meth)acrylate.

Examples of (meth)acrylamides each having a trimethylsiloxy group include 3-[tris(trimethylsiloxy)silyl]propyl (meth)acrylamide, 3-[bis(trimethylsiloxy)methylsilyl]propyl(meth)acrylamide, and 3-[(trimethylsiloxy)dimethylsilyl]propyl(meth)acrylamide.

Examples of styrenes each having a trimethylsiloxy group include [tris(trimethylsiloxy)silyl]styrene, [bis(trimethylsiloxy)methylsilyl]styrene, and [(trimethylsiloxy)dimethylsilyl]styrene.

Examples of vinyl carbamates each having a trimethylsiloxy group include N-[3-[tris(trimethylsiloxy)silyl]propyl] vinyl carbamate, N-[3-[bis(trimethylsiloxy)methylsilyl]propyl] vinyl carbamate, and N-[3-[(trimethylsiloxy)dimethylsilyl]propyl] vinyl carbamate.

When 3-[tris(trimethylsiloxy)silyl]propyl methacryloyloxyethyl succinate is used, polymerization components may be the silicone monomer alone, but typically include any other monomer polymerizable with the silicone monomer. In this case, the usage amount of the silicone monomer is typically from 10 parts by mass to 80 parts by mass, preferably from 40 parts by mass to 80 parts by mass with respect to 100 parts by mass of the monomer composition of the silicone hydrogel contact lens base material.

Further, any other monomer that has been generally used as a monomer to be used for a silicone hydrogel contact lens may be appropriately selected and used.

Preferred examples of the other monomer to be used for the silicone hydrogel contact lens base material for the purpose of controlling the water content of the contact lens include water-soluble monomers, such as (meth)acrylic acid, itaconic acid, crotonic acid, cinnamic acid, vinylbenzoic acid, 2-(meth)acryloyloxyethyl phosphorylcholine, a polyalkylene glycol mono(meth)acrylate, a polyalkylene glycol monoalkyl ether (meth)acrylate, 2-hydroxyethyl (meth) acrylate, 2,3-dihydroxypropyl (meth)acrylate, glycerol (meth)acrylate, N-vinylformamide, N-vinylacetamide, N-methyl-N-vinylacetamide, and N-vinyl-2-pyrrolidone. Of those, from the viewpoint of the controllability of the water content of the contact lens, 2-hydroxyethyl (meth)acrylate and N-vinyl-2-pyrrolidone are more preferred. The usage amount of any such monomer is typically from 10 parts by mass to 50 parts by mass, preferably from 20 parts by mass to 40 parts by mass with respect to 100 parts by mass of the monomer composition of the silicone hydrogel contact lens base material.

Examples of the other monomer to be used for the silicone hydrogel contact lens base material for the purpose of controlling the flexibility of the contact lens include a polyalkylene glycol bis(meth)acrylate, trimethylolpropane tris(meth)acrylate, pentaerythritol tetrakis(meth)acrylate, N,N-dimethyl(meth)acrylamide, N,N-diethyl(meth)acrylamide, N,N-di-n-propyl(meth)acrylamide, N,N-diisopropyl (meth)acrylamide, N,N-di-n-butyl(meth)acrylamide, N-(meth)acryloylmorpholine, N-(meth)acryloylpiperidine, N-vinylcaprolactam, N-vinyloxazolidone, 1-vinylimidazole, N-vinylcarbazole, vinylpyridine, and vinylpyrazine. The usage amount of any such monomer is typically from 10 parts by mass to 50 parts by mass, preferably from 20 parts by mass to 40 parts by mass with respect to 100 parts by mass of the monomer composition of the silicone hydrogel contact lens base material.

Examples of the other monomer to be used for the silicone hydrogel contact lens base material for the purpose of improving the shape maintaining property of the contact lens include: alkyl (meth)acrylates, such as methyl (meth)acrylate and ethyl (meth) acrylate; siloxane macromonomers having carbon-carbon unsaturated bonds at both terminals thereof and polyfunctional (meth) acrylates, such as ethylene glycol dimethacrylate; halogenated alkyl (meth)acrylates, such as trifluoroethyl (meth)acrylate and hexafluoroisopropyl (meth)acrylate; aromatic vinyl monomers, such as styrene, α-methylstyrene, and vinylpyridine; and vinyl esters, such as vinyl acetate. The usage amount of any such monomer is typically from 0.01 part by mass to 30 parts by mass, preferably from 0.1 part by mass to 15 parts by mass with respect to 100 parts by mass of the monomer composition of the silicone hydrogel contact lens base material.

The silicone hydrogel contact lens base material may be produced by mixing the respective monomers, and appropriately adding a thermal polymerization initiator typified by a peroxide or an azo compound, or a photopolymerization initiator to the mixture. When thermal polymerization is performed, a thermal polymerization initiator having a decomposition characteristic optimum for a desired reaction temperature may be selected and used. For example, a peroxide or an azo compound, such as azobisisobutyronitrile, having a 10-hour half-life temperature of from 40° C. to 120° C. may be used. The photopolymerization initiator may be, for example, a carbonyl compound, a sulfur compound, a halogen compound, or a metal salt. Those polymerization initiators may be used alone or as a mixture thereof. Any such initiator is preferably used at a ratio of from 0.05 part by mass to 2 parts by mass with respect to 100 parts by mass of the polymerization components.

When Surface Treatment Object is Silicone Rubber

A silicone monomer to be used for a silicone rubber contact lens base material including, on its surface, the graft polymer containing a constituent unit based on the monomer of the present invention is, for example, a polyorganosiloxane for the purpose of improving the oxygen permeability of the contact lens. For example, both-terminal silanol-modified polydimethylsiloxane having a weight-average molecular weight of 330 (manufactured by Shin-Etsu Chemical Co., Ltd.) is preferred. The usage amount of the silicone monomer is typically from 60 parts by mass to 100 parts by mass, preferably from 75 parts by mass to 95 parts by mass with respect to 100 parts by mass of the monomer composition of the silicone rubber contact lens base material, and is preferably from 75% to 95% in terms of a molar ratio.

The silicone rubber contact lens base material may be produced by mixing the respective constituent units, and appropriately adding a curing catalyst typified by a metal alkoxide to the mixture. Examples of the metal alkoxide may include aluminum isopropoxide and aluminum ethoxide. The curing catalysts may be used alone or as a mixture thereof. The curing catalyst is used at a molar ratio of typically less than 20%, preferably less than 10% with respect to the monomer composition of the silicone rubber contact lens base material.

The production of the silicone rubber contact lens base material may be performed in the presence of a solvent. The solvent is preferably a solvent that does not easily volatilize at room temperature, and is, for example, toluene.

<Method of Producing Silicone Contact Lens Including, on its Surface, Graft Polymer Containing Constituent Unit Based on Monomer of the Present Invention>

Although a method of producing the silicone contact lens including, on its surface, the graft polymer containing a constituent unit based on the monomer of the present invention is not particularly limited as long as a constituent unit represented by the formula (1') is present on the surface of the contact lens base material, a production method including the following steps may be given as an example thereof.

Step of Treating Surface of Contact Lens Base Material

In the method of producing the silicone contact lens of the present invention, in order that the graft polymer chain containing a constituent unit represented by the formula (1') may be formed (coated or chemically modified) on the surface of the contact lens base material, a peroxide (peroxide group) is formed on the surface of the base material.

Step 1: A radical is formed on the surface of the contact lens base material (preferably a water-containing film-shaped contact lens base material). The radical formation method may be performed by, for example, a plasma discharge treatment or excimer light irradiation treatment known per se.

The plasma discharge treatment is performed under reduced pressure or normal pressure (1.3 Pa to 0.1 MPa) and under an oxygen gas atmosphere, an inert gas atmosphere, or an air atmosphere for from 30 seconds to 30 minutes. A pulse frequency is from 20 kHz to 25 kHz, and a high-frequency output is from 10 W to 500 W.

In the excimer light irradiation treatment, the surface is irradiated with vacuum UV light having a wavelength of 172 nm for from 30 seconds to 60 minutes.

Step 2: The contact lens base material having a radical formed on its surface is placed under an oxygen gas atmosphere or an air atmosphere for from 1 minute to 2 hours so that the peroxide (peroxide group) may be formed on the surface.

Step of Bringing Contact Lens Base Material Having Peroxide Group Formed on its Surface and Mixed Solution Containing Branched Polyoxyethylene Derivative (Compound) into Contact with Each Other In the method of producing the silicone contact lens including, on its surface, the graft polymer containing a constituent unit based on the monomer of the present invention, the contact lens base material having a peroxide group formed on its surface and a mixed solution containing a branched polyoxyethylene derivative are brought into contact with each other. The mixed solution containing the branched polyoxyethylene derivative contains at least the monomer of the present invention.

Although a method for the contact is not particularly limited, in order that the mixed solution can be sufficiently in contact with the entirety of the surface of the contact lens base material, the base material is preferably immersed in the mixed solution.

The concentration of the monomer of the present invention in the mixed solution containing the branched polyoxyethylene compound is from 0.01 mol/L to 1.0 mol/L. When the concentration is less than 0.01 mol/L, the surface of the base material cannot be subjected to graft polymerization with such an amount of the monomer that sufficient hydrophilicity and sufficient lubricity can be imparted thereto. When the concentration is more than 1.0 mol/L, the viscosity of the solution increases to make it impossible to subject the surface to uniform graft polymerization. Accordingly, the smoothness of the surface of the base material deteriorates, and hence the base material cannot be used as a contact lens.

Further, the concentration of all the monomers including the monomer of the present invention in the mixed solution containing the branched polyoxyethylene compound is from 0.01 mol/L to 3.5 mol/L. When the concentration is less than 0.01 mol/L, the surface of the base material cannot be subjected to graft polymerization with such an amount of the monomer that sufficient hydrophilicity and sufficient lubricity can be imparted thereto. When the concentration is more than 3.5 mol/L, the viscosity of the solution increases to make it impossible to subject the surface to uniform graft polymerization. Accordingly, the smoothness of the surface of the base material deteriorates, and hence the base material cannot be used as a contact lens.

The mixed solution containing the branched polyoxyethylene compound may contain a hydrophilic monomer (in particular, a hydrophilic ethylenically unsaturated monomer), a crosslinkable monomer, water, an organic solvent, a chain transfer agent, and/or a polymerization sensitizer in addition to the monomer of the present invention.

Examples of the hydrophilic monomer may include, but not particularly limited to, the following. The monomers may be used alone or as a mixture thereof.

(Meth)acrylic acid and various (meth)acrylates, such as methyl (meth)acrylate, ethyl (meth)acrylate, propyl (meth) acrylate, butyl (meth)acrylate, benzyl (meth)acrylate, 2-hydroxyethyl (meth)acrylate, 3-hydroxypropyl (meth)acrylate, 4-hydroxybutyl (meth)acrylate, and 6-hydroxyhexyl (meth) acrylate.

Various polyoxyalkylene mono(meth)acrylates, such as polyoxyethylene methyl ether (meth)acrylate and polyoxypropylene mono(meth)acrylate.

Various polymerizable acrylamides, such as N-vinylformamide, N-vinylacetamide, N-acryloylmorpholine, N-vinyl-2-pyrrolidone, N-vinylpiperidone, N-vinylcaprolactam, N-vinylcaprylolactam, N,N-dimethyl(meth)acrylamide, and N-(meth)acryloyloxyethyl-2-pyrrolidone.

Preferred examples of the hydrophilic monomer may include polyoxyethylene methyl ether methacrylate, polyoxyethylene mono(meth)acrylate, 2-hydroxyethyl methacrylate, N-vinyl-2-pyrrolidone, methacrylic acid, and N,N-dimethylacrylamide.

The concentration of the hydrophilic monomer in the mixed solution containing the branched polyoxyethylene compound is from 0 mol/L to 3.4 mol/L. When the concentration falls within the range, an effect of blending the polyoxyethylene compound can be obtained.

Examples of the crosslinkable monomer may include, but not particularly limited to, the following. The monomers may be used alone or as a mixture thereof.

Ethylene glycol di(meth)acrylate, diethylene glycol di(meth)acrylate, 1,4-bis((meth)acryloyloxy)butane, 1,6-bis ((meth)acryloyloxy)hexane, trimethylolpropane tri(meth) acrylate, pentaerythritol tetra(meth)acrylate, triallyl isocyanurate, diallyl phthalate, and divinylbenzene.

Examples of the organic solvent may include, but not particularly limited to, the following. The organic solvents may be used alone or as a mixture thereof.

Various alcohols, such as ethanol and methanol, acetone, benzene, toluene, acetonitrile, tetrahydrofuran, N,N-dimethylformamide, and methylene chloride.

Examples of the chain transfer agent may include, but not particularly limited to, the following. The chain transfer agents may be used alone or as a mixture thereof.

α-Methylstyrene dimer and various mercaptans, such as n-butyl mercaptan, n-octyl mercaptan, n-lauryl mercaptan, n-dodecyl mercaptan, and t-dodecyl mercaptan.

Halogenated hydrocarbons, such as carbon tetrachloride and carbon tetrabromide.

Other chain transfer agents, such as benzyl dithiobenzoate, 1-phenylethyl dithiobenzoate, 2-phenyl-2-propynyl dithiobenzoate, 1-acetoxyethyl dithiobenzoate, benzyl dithioacetate, t-butyl dithiobenzoate, and 2-cyano-2-propynyl dithiobenzoate.

When the chain transfer agent is incorporated into the mixed solution containing the branched polyoxyethylene compound, a residue derived from the chain transfer agent at a terminal of a graft polymer chain length is produced after graft polymerization in some cases. In such cases, the residue is preferably removed or transformed by being caused to react with a sulfur-containing compound or an alkyl alcohol.

Examples of the polymerization sensitizer may include, but not particularly limited to, compounds each having an anthracene skeleton, such as 9,10-bis(n-octanoyloxy)anthracene. The sensitizers may be used alone or as a mixture thereof.

Step of Subjecting Surface of Contact Lens Base Material to Graft Polymerization with Branched Polyoxyethylene Compound In the method of producing the silicone contact lens of the present invention, a step of subjecting the surface of the contact lens base material to graft polymerization with the branched polyoxyethylene compound may be, for example, the following step, but is not particularly limited thereto.

The graft polymerization is performed as follows: under a state in which the contact lens base material having a peroxide group formed on its surface and the mixed solution containing the branched polyoxyethylene compound are brought into contact with each other, the surface is irradiated with UV light (200 nm to 450 nm) at an irradiance of from 0.5 mW/cm$^2$ to 100 mW/cm$^2$ or from 0.5 mW/cm$^2$ to 15 mW/cm$^2$ for from 1 minute to 1 hour at from 15° C. to 90° C.

After the graft polymerization, an unreacted component is removed as required. A Soxhlet extraction method known per se is used as a method for the removal.

Thus, the silicone contact lens of the present invention can be produced.

[Contact Lens Including Constituent Unit Based on Monomer of the Present Invention]

A contact lens including a constituent unit based on the monomer of the present invention includes in itself a constituent unit represented by the following formula (1').

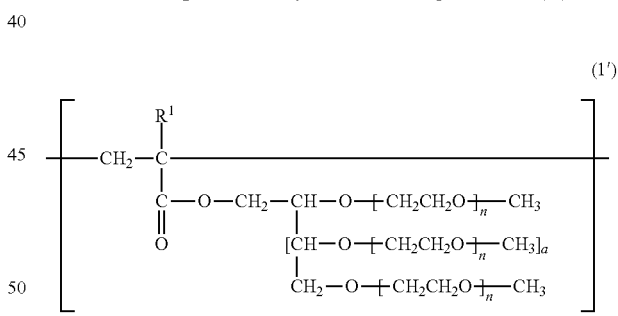

In the formula (1'), n represents from 3 to 1,150, and $R^1$ represents a hydrogen atom or a methyl group. When the n represents 2 or less, sufficient hydrophilicity and sufficient lubricity cannot be imparted to the surface of a contact lens. When the n represents 1,151 or more, the viscosity of the monomer increases to make it difficult to uniformly treat the surface of the contact lens with the monomer, and hence a function of the contact lens is inhibited. The n is not particularly limited as long as the n falls within the range of from 3 to 1,150, and for example, the n may represent from 25 to 800, from 50 to 800, or from 50 to 600, or may represent from 5 to 45, from 15 to 25, from 200 to 250, from 220 to 230, from 425 to 475, or from 447 to 457. The n more preferably represents from 3 to 800, and most preferably represents from 3 to 600.

The usage amount of the monomer of the present invention is typically from 1 part by mass to 40 parts by mass, preferably from 1 part by mass to 20 parts by mass with respect to 100 parts by mass of the monomer composition of the contact lens base material. When the usage amount is less than 1 part by mass, sufficient hydrophilicity and sufficient lubricity cannot be imparted to the surface of the base material, and when the usage amount is more than 40 parts by mass, the shape-maintaining property of the contact lens deteriorates.

A monomer that has been generally used as a monomer for a lens may be appropriately selected and used as any other monomer polymerizable with the contact lens of the present invention.

For example, for controlling the water content of the contact lens, preferred examples of the water-soluble monomer include water-soluble monomers such as (meth)acrylic acid, itaconic acid, crotonic acid, cinnamic acid, vinylbenzoic acid, 2-((meth)acryloyloxy)ethyl-2'-(trimethylammonio)ethyl phosphate, phosphorylcholine (meth)acrylate, a polyalkylene glycol mono(meth)acrylate, a polyalkylene glycol monoalkyl ether (meth)acrylate, 2-hydroxyethyl (meth)acrylate, glycerol (meth) acrylate, N-vinyl-2-pyrrolidone, N-vinylformamide, N-vinylacetamide, and N-methyl-N-vinylacetamide.

Of those, 2-hydroxyethyl (meth)acrylate is particularly preferred for the purpose of controlling the water content. The total usage amount of the water-soluble monomer is typically from 10 parts by mass to 50 parts by mass, preferably from 20 parts by mass to 40 parts by mass with respect to 100 parts by mass of the monomer composition of the silicone hydrogel contact lens base material.

Although the following silicone monomers each intended to improve the oxygen permeability of the contact lens may be given as examples of the other monomer polymerizable with the contact lens of the present invention, 3-[tris(trimethylsiloxy)silyl]propyl methacryloyloxyethyl succinate (see WO 2010/082659 A1) is preferred.

Examples of (meth)acrylates each having a polydimethylsiloxane skeleton include α-methyl-ω-methacryloyloxypropyl polydimethylsiloxane (weight-average molecular weight: 1,000) and α,ω-dimethacryloyloxypropylpolydimethylsiloxane (weight-average molecular weight: 1,000). For example, FM-0711 or FM-7711 sold from JNC Corporation may be used.

Examples of (meth)acrylates each having a trimethylsiloxy group include 3-[tris(trimethylsiloxy)silyl]propyl (meth)acrylate (TRIS), 3-[bis(trimethylsiloxy)methylsilyl] propyl (meth)acrylate, and 3-[(trimethylsiloxy)dimethylsilyl]propyl (meth) acrylate.

Examples of (meth)acrylamides each having a trimethylsiloxy group include 3-[tris(trimethylsiloxy)silyl]propyl (meth)acrylamide, 3-[bis(trimethylsiloxy)methylsilyl]propyl(meth)acrylamide, and 3-[(trimethylsiloxy)dimethylsilyl]propyl(meth)acrylamide.

Examples of styrenes each having a trimethylsiloxy group include [tris(trimethylsiloxy)silyl]styrene, [bis(trimethylsiloxy)methylsilyl]styrene, and [(trimethylsiloxy)dimethylsilyl]styrene.

Examples of vinyl carbamates each having a trimethylsiloxy group include N-[3-[tris(trimethylsiloxy)silyl]propyl] vinyl carbamate, N-[3-[bis(trimethylsiloxy)methylsilyl]propyl] vinyl carbamate, and N-[3-[(trimethylsiloxy)dimethylsilyl]propyl] vinyl carbamate.

The usage amount of the silicone monomer is typically from 10 parts by mass to 80 parts by mass, preferably from 40 parts by mass to 80 parts by mass with respect to 100 parts by mass of the monomer composition of the silicone hydrogel contact lens base material.

Examples of the other monomer polymerizable with the contact lens of the present invention for the purpose of controlling the flexibility of the contact lens include a polyalkylene glycol bis(meth)acrylate, trimethylolpropane tris(meth)acrylate, pentaerythritol tetrakis(meth)acrylate, N,N-dimethylacrylamide, N,N-diethylacrylamide, N,N-di-n-propylacrylamide, N,N-diisopropylacrylamide, N,N-di-n-butylacrylamide, N-acryloylmorpholine, N-acryloylpiperidine, N-vinylcaprolactam, N-vinyloxazolidone, 1-vinylimidazole, N-vinylcarbazole, vinylpyridine, and vinylpyrazine. The usage amount of the monomer for controlling the flexibility of the contact lens is typically from 0 parts by mass to 50 parts by mass, preferably from 5 parts by mass to 40 parts by mass with respect to 100 parts by mass of the monomer composition of the silicone hydrogel contact lens base material.

Examples of the other monomer polymerizable with the contact lens of the present invention for the purpose of improving the shape-maintaining property of the contact lens include: alkyl (meth)acrylates, such as methyl (meth) acrylate and ethyl (meth)acrylate; siloxane macromonomers having carbon-carbon unsaturated bonds at both terminals thereof and polyfunctional (meth) acrylates, such as ethylene glycol dimethacrylate; halogenated alkyl (meth)acrylates, such as trifluoroethyl (meth)acrylate and hexafluoroisopropyl (meth)acrylate; aromatic vinyl monomers, such as styrene, α-methylstyrene, and vinylpyridine; and aliphatic vinyl monomers, such as vinyl acetate. The usage amount of the monomer for improving the shape-maintaining property of the contact lens is typically from 0.01 part by mass to 30 parts by mass, preferably from 0.1 part by mass to 15 parts by mass with respect to 100 parts by mass of the monomer composition of the silicone hydrogel contact lens base material.

The contact lens base material of the present invention can be produced by mixing the respective monomers, and appropriately adding a thermal polymerization initiator typified by a peroxide or an azo compound, or a photopolymerization initiator to the mixture. When thermal polymerization is performed, a thermal polymerization initiator having a decomposition characteristic optimum for a desired reaction temperature may be selected and used. For example, a peroxide or an azo compound, such as azobisisobutyronitrile, having a 10-hour half-life temperature of from 40° C. to 120° C. may be used. The photopolymerization initiator may be, for example, a carbonyl compound, a sulfur compound, a halogen compound, or a metal salt. Those polymerization initiators may be used alone or as a mixture thereof. Any such initiator is preferably used at a ratio of from 0.05 part by mass to 2 parts by mass with respect to 100 parts by mass of the polymerization components.

After the polymerization, an unreacted component is removed as required.

Thus, the silicone contact lens including a constituent unit based on the monomer of the present invention can be produced.

The present invention is also directed to a method of producing a silicone contact lens including, on its surface, a graft polymer containing a constituent unit represented by the following formula (1'):

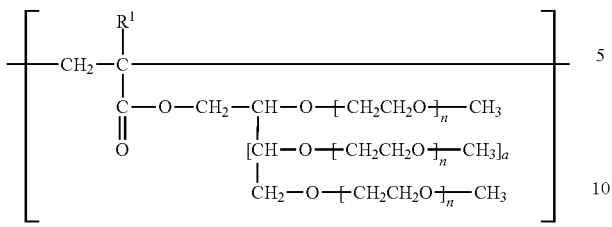

(1')

where n represents from 3 to 1,150, a represents 0 or 2, and $R^1$ represents a hydrogen atom or a methyl group.

The production method includes the following steps:

(I) a step of treating the surface of a contact lens base material;

(II) a step of bringing the contact lens base material obtained in the step (I) and a mixed solution containing a branched polyoxyethylene compound (monomer represented by the following formula (1)) into contact with each other; and (III) a step of subjecting the surface of the contact lens base material to graft polymerization with the branched polyoxyethylene compound.

The production method may further include the following step:

(IV) a step of removing an unreacted component.

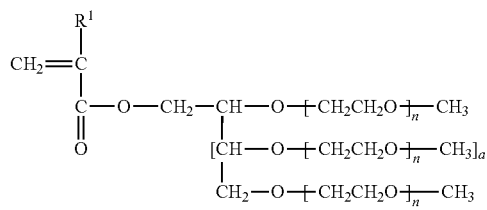

(1)

where n represents from 3 to 1,150, a represents 0 or 2, and $R^1$ represents a hydrogen atom or a methyl group.

The present invention is also directed to a method of producing a contact lens including a constituent unit represented by the following formula (1'):

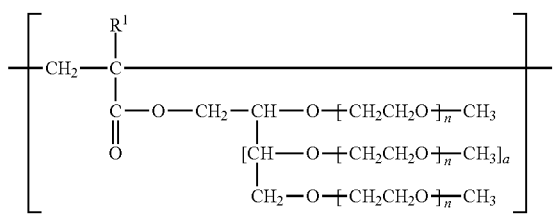

(1')

where n represents from 3 to 1,150, a represents 0 or 2, and $R^1$ represents a hydrogen atom or a methyl group.

The production method includes the following steps:

(I) a step of mixing a monomer represented by the following formula (1), any other monomer polymerizable with the contact lens of the present invention, and a polymerization initiator; and (II) a step of polymerizing the mixture obtained in the step (I).

The production method may further include the following step:

(III) a step of removing an unreacted component.

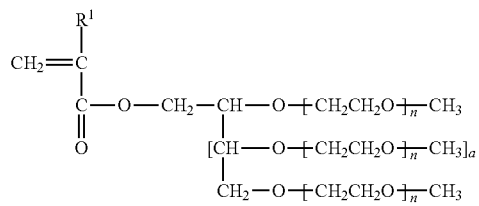

(1)

where n represents from 3 to 1,150, a represents 0 or 2, and $R^1$ represents a hydrogen atom or a methyl group.

The present invention is also directed to a surface treatment agent for a contact lens, including a branched polyoxyethylene compound represented by the following formula (1):

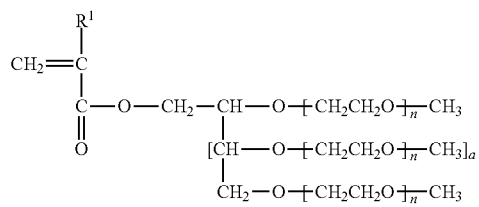

(1)

where n represents from 3 to 1,150, a represents 0 or 2, and $R^1$ represents a hydrogen atom or a methyl group.

The present invention is also directed to a surface treatment method for a contact lens, including using a branched polyoxyethylene compound represented by the following formula (1):

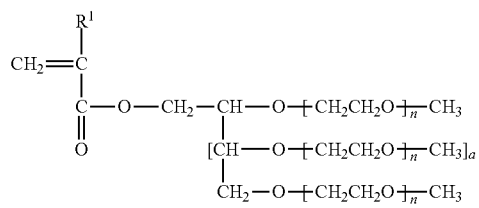

(1)

where n represents from 3 to 1,150, a represents 0 or 2, and $R^1$ represents a hydrogen atom or a methyl group.

The present invention is also directed to a branched polyoxyethylene compound for a surface treatment of a contact lens, which is represented by the following formula (1):

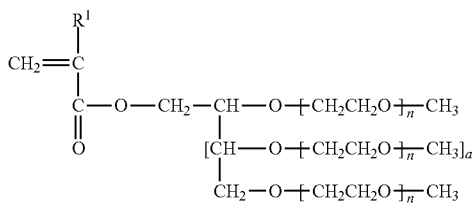

(1)

where n represents from 3 to 1,150, a represents 0 or 2, and $R^1$ represents a hydrogen atom or a methyl group.

The present invention is also directed to a use of a branched polyoxyethylene compound represented by the following formula (1) as production of a surface treatment agent for a contact lens:

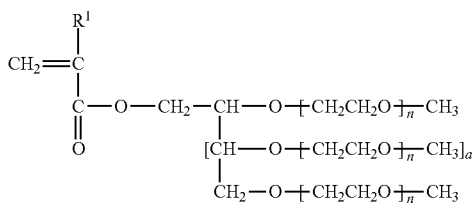

(1)

where n represents from 3 to 1,150, a represents 0 or 2, and $R^1$ represents a hydrogen atom or a methyl group.

EXAMPLES

The branched polyoxyethylene compound of the present invention, a silicone contact lens including, on its surface, a constituent unit based on the compound, and a contact lens including the constituent unit are described in more detail on the basis of Examples.

Example 1-1

(Synthesis of Polyoxyethylene Compound 1)

200 g (10 mmol) of the polyoxyethylene derivative A represented by the formula (2) and having a weight-average molecular weight of 20,000, and 800 g of toluene were loaded into a 1-liter four-necked flask mounted with a temperature gauge, a nitrogen-blowing tube, a stirring machine, a Dean-Stark tube, and a cooling tube. While the mixture was stirred and nitrogen was blown into the flask, the mixture was warmed to 40° C. to dissolve the derivative in toluene. The temperature of the solution was increased to 110° C., and about 200 g of a fraction was extracted while the solution was subjected to azeotropy with toluene, followed by dehydration. The residue was cooled to 30° C., and 15.94 g (0.1575 mol) of triethylamine and 13.58 g (0.15 mol) of acryloyl chloride were added to the residue. The mixture was subjected to a reaction at 40° C. for 6 hours.

After the reaction, triethylamine hydrochloride in the solvent was separated by filtration, and then the filtrate was cooled to room temperature. 600 g of ethyl acetate and 600 g of n-hexane were added to crystallize the filtrate. After the crystal had been collected by filtration, the crystal was dissolved in 1.6 kg of ethyl acetate at 35° C., and the solution was cooled to room temperature. After that, 400 g of n-hexane was added to crystallize the solution. The crystal was collected by filtration and washed with 1.2 kg of n-hexane. The crystal was collected by filtration and dried under a vacuum to provide 167 g of a polyoxyethylene compound 1 represented by the following formula (3) and having a weight-average molecular weight of 20,000. The weight-average molecular weight of the synthesized polyoxyethylene compound 1 was determined by gel permeation chromatography (GPC). In detail, the weight-average molecular weight was measured as follows: a differential refractometer was used as a detector, three columns, i.e., SHODEX KF801L, KF803L, and KF804L (8 mmφ×300 mm) connected in series were used as a GPC column, the temperature of a column oven was set to 40° C., tetrahydrofuran was used as an eluent, the flow rate of the eluent was set to 1 mL/min, the concentration of the sample was set to 0.1 mass %, and the injection volume of the sample was set to 0.1 mL. In addition, the molecular structure of the resultant compound was identified by $^1$H-NMR. The results of the $^1$H-NMR analysis are described below. A polymerization degree n of the sample was calculated by dividing the weight-average molecular weight determined from the GPC by the formula weight thereof.

$^1$H-NMR (CDCl$_3$) δ (ppm): 3.38 (6H, s, —(CH$_2$CH$_2$O)$_n$—C$\underline{H}_3$), 3.47-4.00 (1.97 kH, m, —C$\underline{H}_2$O(CH$_2$CH$_2$O)$_n$—CH$_3$, —CH$_2$C$\underline{H}$O(CH$_2$CH$_2$O)$_n$—CH$_3$), 4.17-4.39 (2H, m, —COOC$\underline{H}_2$—), 5.84 (1H, m, —CH=C$\underline{H}_2$), 6.16 (1H, m, —CH=C$\underline{H}_2$), 6.38 (1H, m, —C$\underline{H}$=CH$_2$).

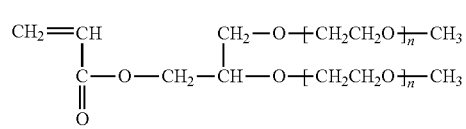

(3)

n = 225

Example 1-2

(Synthesis of Polyoxyethylene Compound 2)

200 g (10 mmol) of the polyoxyethylene derivative A represented by the formula (2) and having a weight-average molecular weight of 20,000, and 800 g of toluene were loaded into a 1-liter four-necked flask mounted with a temperature gauge, a nitrogen-blowing tube, a stirring machine, a Dean-Stark tube, and a cooling tube. While the mixture was stirred and nitrogen was blown into the flask, the mixture was warmed to 40° C. to dissolve the derivative in toluene. The temperature of the solution was increased to 110° C., and about 200 g of a fraction was extracted while the solution was subjected to azeotropy with toluene, followed by dehydration. The residue was cooled to 30° C., and 15.94 g (0.1575 mol) of triethylamine and 15.68 g (0.15 mol) of methacryloyl chloride were added to the residue. The mixture was subjected to a reaction at 60° C. for 10 hours.

After the reaction, triethylamine hydrochloride in the solvent was separated by filtration, and then the filtrate was cooled to room temperature. 600 g of ethyl acetate and 600 g of n-hexane were added to crystallize the filtrate. After the crystal had been collected by filtration, the crystal was dissolved in 1.6 kg of ethyl acetate at 35° C., and the solution was cooled to room temperature. After that, 400 g of n-hexane was added to crystallize the solution. The crystal was collected by filtration and washed with 1.2 kg of n-hexane. The crystal was collected by filtration and dried under a vacuum to provide 160 g of a polyoxyethylene compound 2 represented by the following formula (4) and having a weight-average molecular weight of 20,000. The weight-average molecular weight of the synthesized polyoxyethylene compound 2 was determined through the use of GPC by the same method as that of Example 1-1. In addition, its molecular structure was determined by $^1$H-NMR. The results of the $^1$H-NMR analysis are described below.

$^1$H-NMR (CDCl$_3$) δ (ppm): 1.95 (3H, s, —C(CH$_3$)=CH$_2$), 3.38 (6H, s, —(CH$_2$CH$_2$O)$_n$—CH$_3$), 3.47-4.00 (1.97 kH, m, —CH$_2$O(CH$_2$CH$_2$O)$_n$—CH$_3$, —CH$_2$CHO(CH$_2$CH$_2$O)$_n$—CH$_3$), 4.13-4.39 (2H, m, —COOCH$_2$—), 5.57 (1H, m, —C(CH$_3$)=CH$_2$), 6.11 (1H, m, —C(CH$_3$)=CH$_2$).

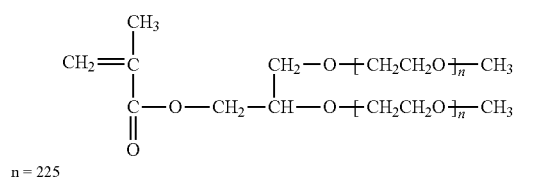

(4)

n = 225

Example 1-3

(Synthesis of Polyoxyethylene Compound 3)

200 g (5 mmol) of the polyoxyethylene derivative B represented by the formula (5) and having a weight-average molecular weight of 40,000, and 800 g of toluene were loaded into a 1-liter four-necked flask mounted with a temperature gauge, a nitrogen-blowing tube, a stirring machine, a Dean-Stark tube, and a cooling tube. While the mixture was stirred and nitrogen was blown into the flask, the mixture was warmed to 40° C. to dissolve the derivative in toluene. The temperature of the solution was increased to 110° C., and about 200 g of a fraction was extracted while the solution was subjected to azeotropy with toluene, followed by dehydration. The residue was cooled to 30° C., and 15.94 g (0.1575 mol) of triethylamine and 13.58 g (0.15 mol) of acryloyl chloride were added to the residue. The mixture was subjected to a reaction at 40° C. for 6 hours.

After the reaction, triethylamine hydrochloride in the solvent was separated by filtration, and then the filtrate was cooled to room temperature. 600 g of ethyl acetate and 600 g of n-hexane were added to crystallize the filtrate. After the crystal had been collected by filtration, the crystal was dissolved in 1.6 kg of ethyl acetate at 35° C., and the solution was cooled to room temperature. After that, 400 g of n-hexane was added to crystallize the solution. The crystal was collected by filtration and washed with 1.2 kg of n-hexane. The crystal was collected by filtration and dried under a vacuum to provide 151 g of a polyoxyethylene compound 3 represented by the following formula (6) and having a weight-average molecular weight of 40,000. The weight-average molecular weight of the synthesized polyoxyethylene compound 3 was determined through the use of GPC by the same method as that of Example 1-1. In addition, its molecular structure was determined by $^1$H-NMR. The results of the $^1$H-NMR analysis are described below.

$^1$H-NMR (CDCl$_3$) δ (ppm): 3.38 (6H, s, —(CH$_2$CH$_2$O)$_n$—CH$_3$), 3.47-4.00 (4.05 kH, m, —CH$_2$O(CH$_2$CH$_2$O)$_n$—CH$_3$, —CH$_2$CHO(CH$_2$CH$_2$O)$_n$—CH$_3$)), 4.17-4.39 (2H, m, —COOCH$_2$—), 5.84 (1H, m, —CH=CH$_2$), 6.15 (1H, m, —CH=CH$_2$), 6.39 (1H, m, —CH=CH$_2$).

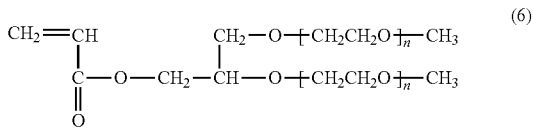

(6)

n = 452

Example 1-4

(Synthesis of Polyoxyethylene Compound 4)

200 g (5 mmol) of the polyoxyethylene derivative C represented by the formula (7) and having a weight-average molecular weight of 40,000, and 800 g of toluene were loaded into a 1-liter four-necked flask mounted with a temperature gauge, a nitrogen-blowing tube, a stirring machine, a Dean-Stark tube, and a cooling tube. While the mixture was stirred and nitrogen was blown into the flask, the mixture was warmed to 40° C. to dissolve the derivative in toluene. The temperature of the solution was increased to 110° C., and about 200 g of a fraction was extracted while the solution was subjected to azeotropy with toluene, followed by dehydration. The residue was cooled to 30° C., and 15.94 g (0.1575 mol) of triethylamine and 13.58 g (0.15 mol) of acryloyl chloride were added to the residue. The mixture was subjected to a reaction at 40° C. for 6 hours.

After the reaction, triethylamine hydrochloride in the solvent was separated by filtration, and then the filtrate was cooled to room temperature. 600 g of ethyl acetate and 600 g of n-hexane were added to crystallize the filtrate. After the crystal had been collected by filtration, the crystal was dissolved in 1.6 kg of ethyl acetate at 35° C., and the solution was cooled to room temperature. After that, 400 g of n-hexane was added to crystallize the solution. The crystal was collected by filtration and washed with 1.2 kg of n-hexane. The crystal was collected by filtration and dried under a vacuum to provide 162 g of a polyoxyethylene compound 4 represented by the following formula (8) and having a weight-average molecular weight of 40,000. The weight-average molecular weight of the synthesized polyoxyethylene compound 4 was determined through the use of GPC by the same method as that of Example 1-1. In addition, its molecular structure was determined by $^1$H-NMR. The results of the $^1$H-NMR analysis are described below.

$^1$H-NMR (CDCl$_3$) δ (ppm): 3.38 (12H, s, —(CH$_2$CH$_2$O)$_n$—CH$_3$), 3.47-4.00 (4.00 kH, m, —CH$_2$O(CH$_2$CH$_2$O)$_n$—CH$_3$, —(CHO(CH$_2$CH$_2$O)$_n$—CH$_3$)$_3$), 4.20-4.39 (2H, m, —COOCH$_2$—), 5.84 (1H, m, —CH=CH$_2$), 6.15 (1H, m, —CH=CH$_2$), 6.39 (1H, m, —CH=CH$_2$).

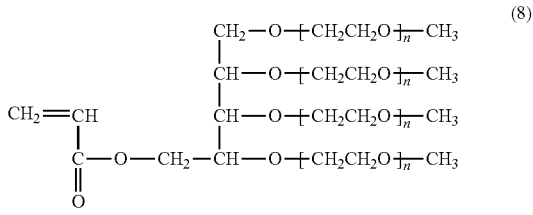

(8)

n = 225

Example 1-5

(Synthesis of Polyoxyethylene Compound 5)

200 g (0.1 mol) of the polyoxyethylene derivative D represented by the formula (10) and having a weight-average molecular weight of 2,000, and 800 g of toluene were loaded into a 1-liter four-necked flask mounted with a temperature gauge, a nitrogen-blowing tube, a stirring machine, a Dean-Stark tube, and a cooling tube. While the mixture was stirred and nitrogen was blown into the flask, the mixture was warmed to 40° C. to dissolve the derivative in toluene. The temperature of the solution was increased to 110° C., and about 200 g of a fraction was extracted while the solution was subjected to azeotropy with toluene, followed by dehydration. The residue was cooled to 30° C., and 20.23 g (0.2 mol) of triethylamine and 13.58 g (0.15 mol) of acryloyl chloride were added to the residue. The mixture was subjected to a reaction at 40° C. for 6 hours.

After the reaction, triethylamine hydrochloride in the solvent was separated by filtration, and then the filtrate was cooled to room temperature. 600 g of ethyl acetate and 600 g of n-hexane were added to crystallize the filtrate. After the crystal had been collected by filtration, the crystal was dissolved in 1.6 kg of ethyl acetate at 35° C., and the solution was cooled to room temperature. After that, 400 g of n-hexane was added to crystallize the solution. The crystal was collected by filtration and washed with 1.2 kg of n-hexane. The crystal was collected by filtration and dried under a vacuum to provide 167 g of a polyoxyethylene compound 5 represented by the following formula (11) and having a weight-average molecular weight of 20,000. The weight-average molecular weight of the synthesized polyoxyethylene compound 5 was determined by gel permeation chromatography (GPC). In detail, the weight-average molecular weight was measured as follows: a differential refractometer was used as a detector, three columns, i.e., SHODEX KF801L, KF803L, and KF804L (8 mmφ×300 mm) connected in series were used as a GPC column, the temperature of a column oven was set to 40° C., tetrahydrofuran was used as an eluent, the flow rate of the eluent was set to 1 mL/min, the concentration of the sample was set to 0.1 mass %, and the injection volume of the sample was set to 0.1 mL. In addition, the molecular structure of the resultant compound was identified by $^1$H-NMR. The results of the $^1$H-NMR analysis are described below. A polymerization degree n of the sample was calculated by dividing the weight-average molecular weight determined from the GPC by the formula weight thereof.

$^1$H-NMR (CDCl$_3$) δ (ppm): 3.38 (6H, s, —C$\underline{H}_2$CH$_2$O)$_n$—C$\underline{H}_3$), 3.47-4.00 (1.97 kH, m, —C$\underline{H}_2$O(C$\underline{H}_2$C$\underline{H}_2$O)$_n$—CH$_3$, —CH$_2$C$\underline{H}$O(C$\underline{H}_2$C$\underline{H}_2$O)$_n$—CH$_3$), 4.17-4.39 (2H, m, —COOC$\underline{H}_2$—), 5.84 (1H, m, —C$\underline{H}$=CH$_2$), 6.16 (1H, m, —CH=C$\underline{H}_2$), 6.38 (1H, m, —C$\underline{H}$=CH$_2$).

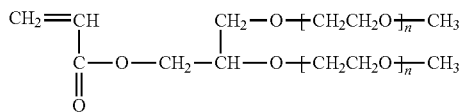

(11)

n = 20

<Method of Evaluating Surface Hydrophilicity>

The hydrophilicity of the surface of a contact lens was evaluated by the following procedure. The contact lens was removed from a preservation solution, and was washed in 200 mL of physiological saline three times in order for the preservation solution adhering to the surface of the contact lens to be removed therefrom. In a windless room, the contact lens was removed from the physiological saline and placed in front of lighting. A time period (WBUT) required for a water film to break to expose the surface of the contact lens was recorded by visual observation. A score of "0" was given to a case in which the WBUT was less than 5 seconds, a score of "1" was given to a case in which the WBUT was 5 seconds or more and less than 15 seconds, and a score of "2" was given to a case in which the WBUT was 15 seconds or more.

<Method of Evaluating Surface Lubricity>

The lubricity of the surface of a contact lens was evaluated by the following procedure. SEED 1 day Fine (trademark) (manufactured by SEED Co., Ltd.) and PROCLEAR 1 day (trademark) (manufactured by CooperVision Japan, Inc.) were used as the standards of a lubricity test. A produced water-containing film was immersed in 10 mL of physiological saline, and was shaken overnight. The water-containing film that had been immersed in the physiological saline and shaken overnight was removed and mounted on a forefinger, followed by the evaluation of its lubricity. The lubricity evaluation was performed as follows: the lubricity was turned into a score in the range of from 1 point to 10 points while the evaluation score of the SEED 1 day Fine (trademark) (manufactured by SEED Co., Ltd.) immediately after its removal from a blister pack was defined as 2 points, and the evaluation score of the PROCLEAR 1 day (trademark) (manufactured by CooperVision Japan, Inc.) was defined as 8 points.

Example 2-1

(Silicone Contact Lens Subjected to Surface Treatment with Polyoxyethylene Compound 1)

60 Parts by mass of a silicone monomer represented by the following formula (9) (3-[tris(trimethylsiloxy)silyl]propyl methacryloyloxyethyl succinate), 40 parts by mass of 2-hydroxyethyl methacrylate, 0.5 part by mass of ethylene glycol dimethacrylate, and 0.5 part by mass of azobisisobutyronitrile were mixed and dissolved. The solution was flowed into a cell sandwiched between a glass plate and a polypropylene plate through the use of a polyethylene terephthalate sheet having a thickness of 0.1 mm as a spacer. After an oven had been purged with nitrogen, the solution was heated at 100° C. for 2 hours to be polymerized, followed by molding into a film shape. Items to be evaluated in the present invention are hydrophilicity and lubricity, and hence the polymerized product was molded not into a lens shape but into the film shape for facilitating the performance of an experiment. After the polymerization, the cured film was removed from the cell, and was immersed in a mixed liquid containing ethanol (EtOH) and ion-exchanged water at a ratio of 3/1 for 12 hours, and in ion-exchanged water for 12 hours to produce a water-containing film. The produced water-containing film was placed in a discharging apparatus, and a pressure in a chamber was reduced to about 2.66 Pa. After that, a plasma discharge treatment was performed under an oxygen gas atmosphere at about 13.3 Pa for 10 minutes (frequency: 13.56 MHz, high-frequency output: 50 W). After that, a peroxide (peroxide group) was produced on the surface of the water-containing film by storing the water-containing film under an oxygen gas atmosphere for 10 minutes or more.

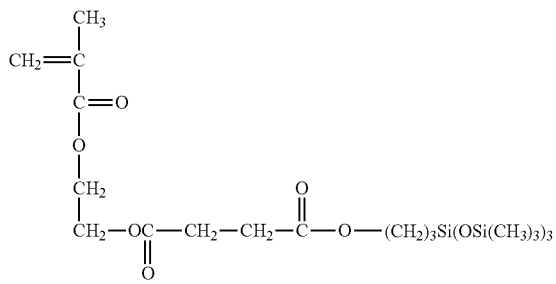

(9)

Next, the produced water-containing film was immersed in a composition containing 20 w/w % (0.0108 mol/L) of the polyoxyethylene compound 1, 0.05 w/w % of 9,10-bis(n-octanoyloxy)anthracene, and 79.95 w/w % of toluene, followed by purging with nitrogen. After that, a coating film of a hydrophilic graft polymer was formed on the surface of the water-containing film by irradiating the surface with UV light (wavelength: 395 nm) at an irradiance of 50 mW/cm$^2$ under room temperature for 2 minutes. After the completion of the reaction, the water-containing film was removed from the composition and washed with distilled water, and extraction was performed with distilled water in a Soxhlet extractor for 16 hours to remove an unreacted residue from the water-containing film. Thus, a water-containing film including, on its surface, a graft polymer chain containing a constituent unit represented by the formula (1') was produced. The water-containing film produced as described in the foregoing was evaluated for its surface hydrophilicity and surface lubricity. The results are shown in Table 1.

The term "PEG400 monomethacrylate" means polyoxyethylene methyl ether methacrylate (molecular weight: 400).

Example 2-2 to Example 2-11

Water-containing films each including, on its surface, a graft polymer chain containing a constituent unit represented by the formula (1') were each produced in accordance with the same procedure as that of Example 1 except that components whose kinds and amounts were shown in Table 1 were used. The surface hydrophilicity and surface lubricity of each of Examples are shown in Table 1.

As can be seen from the results shown in Table 1, in each of Examples 2-1, 2-2, 2-5, 2-8, 2-10, and 2-11 (contact lenses each including, on its surface, a graft polymer chain derived only from the monomer of the present invention), and Examples 2-3, 2-4, 2-6, 2-7, and 2-9 (contact lenses each including, on its surface, a graft polymer chain derived from the monomer of the present invention and a hydrophilic monomer), the water-containing film including, on its surface, the graft polymer chain containing a constituent unit represented by the formula (1') showed excellent surface hydrophilicity and excellent surface lubricity.

Comparative Example 1-1

(Silicone Contact Lens Subjected to Surface Treatment with Low Concentration of Polyoxyethylene Compound 1)

A water-containing film was produced in the same manner as in Example 2-1. The produced water-containing film was immersed in a composition containing a low concentration, i.e., 5 w/w % (0.0023 mol/L) of the polyoxyethylene compound 1, 0.05 w/w % of 9,10-bis(n-octanoyloxy)anthracene, and 94.95 w/w % of toluene, followed by purging with nitrogen. After that, a coating film of a hydrophilic graft polymer was formed on the surface of the water-containing film by irradiating the surface with UV light (wavelength: 395 nm) at an irradiance of 50 mW/cm$^2$ under room temperature for 2 minutes. After the completion of the reaction, the water-containing film was removed from the composition and washed with distilled water, and extraction was performed with distilled water in a Soxhlet extractor for 16 hours to remove an unreacted residue from the water-containing film. The film produced as described in the foregoing was evaluated for its surface hydrophilicity and surface lubricity. The results are shown in Table 2.

Comparative Example 1-2 and Comparative Example 1-3

(Silicone Contact Lens Subjected to Surface Treatment with Graft Polymer Derived from Hydrophilic Monomer)

Water-containing films subjected to surface treatments with various compositions were each produced in accordance with the same procedure as that of Comparative Example 1 except that components whose kinds and amounts were shown in Table 2 were used. The surface hydrophilicity and surface lubricity of each of Comparative Examples are shown in Table 2.

It was confirmed from the foregoing results that the silicone contact lens of the present invention including, on its surface, a graft polymer chain containing a constituent unit represented by the formula (1') had excellent surface hydrophilicity and excellent surface lubricity.

As can be seen from the results shown in Table 2, the results of Comparative Example 1-1 were as follows: the blending amount of the polyoxyethylene compound 1 was less than 0.01 mol/L, and hence the surface hydrophilicity and surface lubricity of the water-containing film reduced. The results of each of Comparative Examples 1-2 and 1-3 were as follows: the water-containing film did not have, on its surface, any graft polymer chain containing a constituent unit represented by the formula (1'), and hence the surface hydrophilicity and surface lubricity of the water-containing film reduced.

Example 3-1

(Contact Lens Including Polyoxyethylene Compound 1 as Constituent Unit)

20 Parts by mass of the polyoxyethylene compound 1, 50 parts by mass of 3-[tris(trimethylsiloxy)silyl]propyl methacryloyloxyethyl succinate, 29 parts by mass of 2-hydroxyethyl methacrylate, 0.5 part by mass of ethylene glycol dimethacrylate, and 0.5 part by mass of azobisisobutyronitrile were mixed and dissolved. The solution was flowed into a cell sandwiched between a glass plate and a polypropylene plate through the use of a polyethylene terephthalate sheet having a thickness of 0.1 mm as a spacer. After an oven had been purged with nitrogen, the solution was heated at 100° C. for 2 hours to be polymerized, followed by molding into a film shape. Items to be evaluated in the present invention are hydrophilicity and lubricity, and hence the polymerized product was molded not into a lens shape but into the film shape for facilitating the performance of an experiment. After the polymerization, the cured film was removed from the cell, and was immersed in a mixed liquid containing ethyl alcohol (EtOH) and ion-exchanged water at a ratio of 3/1 for 12 hours, and in ion-exchanged water for 12 hours to produce a water-containing film. The water-containing film produced as described in the foregoing was evaluated for its surface hydrophilicity and surface lubricity. The results are shown in Table 3.

The term "TRIS" means 3-[tris (trimethylsiloxy) silyl] propyl methacrylate.

Example 3-2 to Example 3-9

Water-containing films were each produced in accordance with the same procedure as that of Example 3-1 except that components whose kinds and amounts were shown in Table 3 were used. The surface hydrophilicity and surface lubricity of each of Examples are shown in Table 3.

As can be seen from the results shown in Table 3, in each of Examples 3-1 to 3-9, the water-containing film including a constituent unit represented by the formula (1') showed excellent surface hydrophilicity and excellent surface lubricity.

Comparative Example 2-1

A water-containing film was produced in the same manner as in Example 3-1 except that components whose kinds and amounts were shown in Table 4 were used.

Comparative Example 2-2 to Comparative Example 2-4

(Surface Treatment with Graft Polymer Derived from Hydrophilic Monomer)

Water-containing films were each produced in accordance with the same procedure as that of Comparative Example 2-1 except that components whose kinds and amounts were shown in Table 4 were used. The surface hydrophilicity and surface lubricity of each of Comparative Examples are shown in Table 4.

As can be seen from the results shown in Table 4, the results of Comparative Example 2-1 were as follows: when the polyoxyethylene methyl ether methacrylate that was not represented by the formula (1) and had a weight-average molecular weight of 400 was used as a polyoxyethylene compound instead of the monomer of the present invention, the surface hydrophilicity and surface lubricity of the water-containing film were low. The results of each of Comparative Examples 2-2 to 2-4 were as follows: when the water-containing film did not include any constituent unit based on a polyoxyethylene compound, the surface hydrophilicity and surface lubricity of the water-containing film were low.

As can be seen from Comparative Examples 2-1 to 2-4 described above, the following results were obtained: when a water-containing film did not include any constituent unit represented by the formula (1'), the surface hydrophilicity and surface lubricity of the water-containing film were low.

It was confirmed that a contact lens including a constituent unit based on the monomer of the present invention (constituent unit represented by the formula (1')) had excellent surface hydrophilicity and excellent surface lubricity.

It was confirmed from the foregoing results that the silicone contact lens of the present invention including, on its surface, a graft polymer chain containing a constituent unit represented by the formula (1'), and the contact lens thereof including a constituent unit represented by the formula (1') each had excellent surface hydrophilicity and excellent surface lubricity.

TABLE 1

| Component | Example 2-1 Blending amount (w/w %) | Example 2-2 Blending amount (w/w %) | Example 2-3 Blending amount (w/w %) | Example 2-4 Blending amount (w/w %) | Example 2-5 Blending amount (w/w %) | Example 2-6 Blending amount (w/w %) |
|---|---|---|---|---|---|---|
| Polyoxyethylene compound 1 | 20 | 40 | 25 | 20 | — | — |
| Polyoxyethylene compound 2 | — | — | — | — | 20 | 20 |
| Polyoxyethylene compound 3 | — | — | — | — | — | — |
| Polyoxyethylene compound 4 | — | — | — | — | — | — |
| Polyoxyethylene compound 5 | — | — | — | — | — | — |
| PEG400 monomethacrylate | — | — | — | 10 | — | — |
| 2-Hydroxyethyl methacrylate | — | — | 10 | 5 | — | — |
| N-Vinyl-2-pyrrolidone | — | — | — | — | — | 5 |
| Methacrylic acid | — | — | — | — | — | 5 |
| N,N-Dimethylacrylamide | — | — | — | — | — | 10 |
| 9,10-Bis(n-octanoyloxy)anthracene | 0.05 | 0.05 | 0.05 | 0.05 | 0.05 | 0.05 |
| Toluene | 79.95 | 59.95 | 64.95 | 64.95 | 79.95 | 59.95 |
| Polyoxyethylene compound 1 Molar concentration (mol/L) | 0.0108 | 0.0289 | 0.0167 | 0.0133 | 0.0108 | 0.0145 |
| Total monomer molar concentration (mol/L) | 0.0108 | 0.0289 | 1.0424 | 0.8599 | 0.0108 | 2.9639 |
| Surface hydrophilicity | 2 | 2 | 2 | 2 | 2 | 2 |
| Surface lubricity | 10 | 10 | 10 | 9 | 10 | 10 |

| Component | Example 2-7 Blending amount (w/w %) | Example 2-8 Blending amount (w/w %) | Example 2-9 Blending amount (w/w %) | Example 2-10 Blending amount (w/w %) | Example 2-11 Blending amount (w/w %) |
|---|---|---|---|---|---|
| Polyoxyethylene compound 1 | — | — | — | — | — |
| Polyoxyethylene compound 2 | — | — | — | — | — |
| Polyoxyethylene compound 3 | 30 | 40 | — | — | — |
| Polyoxyethylene compound 4 | — | — | 30 | — | — |
| Polyoxyethylene compound 5 | — | — | — | 20 | 45 |
| PEG400 monomethacrylate | — | — | 5 | — | — |
| 2-Hydroxyethyl methacrylate | 5 | — | — | — | — |
| N-Vinyl-2-pyrrolidone | — | — | 5 | — | — |

TABLE 1-continued

| Component | | | | | |
|---|---|---|---|---|---|
| Methacrylic acid | — | — | — | — | — |
| N,N-Dimethylacrylamide | — | — | — | — | — |
| 9,10-Bis(n-octanoyloxy)anthracene | 0.05 | 0.05 | 0.05 | 0.05 | 0.05 |
| Toluene | 64.95 | 59.95 | 59.95 | 79.95 | 54.95 |
| Polyoxyethylene compound 1 Molar concentration (mol/L) | 0.0100 | 0.0145 | 0.0108 | 0.1084 | 0.3550 |
| Total monomer molar concentration (mol/L) | 0.5229 | 0.0145 | 0.8422 | 0.1084 | 0.3550 |
| Surface hydrophilicity | 2 | 2 | 2 | 2 | 2 |
| Surface lubricity | 9 | 9 | 9 | 10 | 10 |

TABLE 2

| Component | Comparative Example 1-1 Blending amount (w/w %) | Comparative Example 1-2 Blending amount (w/w %) | Comparative Example 1-3 Blending amount (w/w %) |
|---|---|---|---|
| Polyoxyethylene compound 1 | 5 | — | — |
| 2-Hydroxyethyl methacrylate | — | 25 | 10 |
| N-Vinyl-2-pyrrolidone | — | 15 | — |
| Methacrylic acid | — | 10 | 10 |
| N,N-Dimethylacrylamide | — | — | 10 |
| 9,10-Bis(n-octanoyloxy)anthracene | 0.05 | 0.05 | 0.05 |
| Toluene | 94.95 | 49.95 | 69.95 |
| Polyoxyethylene compound 1 Molar concentration (mol/L) | 0.0023 | 0.0000 | 0.0000 |
| Total monomer molar concentration (mol/L) | 0.0023 | 7.6932 | 3.6425 |
| Surface hydrophilicity | 1 | 0 | 0 |
| Surface lubricity | 4 | 3 | 2 |

TABLE 3

| Component | Example 3-1 Blending amount (w/w %) | Example 3-2 Blending amount (w/w %) | Example 3-3 Blending amount (w/w %) | Example 3-4 Blending amount (w/w %) | Example 3-5 Blending amount (w/w %) | Example 3-6 Blending amount (w/w %) | Example 3-7 Blending amount (w/w %) | Example 3-8 Blending amount (w/w %) | Example 3-9 Blending amount (w/w %) |
|---|---|---|---|---|---|---|---|---|---|
| Polyoxyethylene compound 1 | 20 | 39 | 1 | — | — | — | — | — | — |
| Polyoxyethylene compound 2 | — | — | — | 20 | — | — | — | — | — |
| Polyoxyethylene compound 3 | — | — | — | — | 10 | — | — | — | — |
| Polyoxyethylene compound 4 | — | — | — | — | — | 5 | — | — | — |
| Polyoxyethylene compound 5 | — | — | — | — | — | — | 20 | 1 | 39 |
| 2-Hydroxyethyl methacrylate | 29 | 10 | 38 | 24 | 19 | 24 | 29 | 20 | 10 |
| N-Vinyl-2-pyrrolidone | — | 10 | — | — | 10 | 5 | 10 | — | 10 |
| Methacrylic acid | — | — | — | 5 | — | — | — | — | — |
| N,N-Dimethylacrylamide | — | — | — | — | — | 5 | — | — | — |
| 3-[Tris(trimethylsiloxy)silyl]propyl methacryloyloxyethyl succinate | 50 | 40 | 60 | 50 | — | 60 | — | 78 | 40 |
| TRIS | — | — | — | — | 60 | — | 40 | — | — |
| Ethylene glycol dimethacrylate | 0.5 | 0.5 | 0.5 | 0.5 | 0.5 | 0.5 | 0.5 | 0.5 | 0.5 |
| Azobisisobutyronitrile | 0.5 | 0.5 | 0.5 | 0.5 | 0.5 | 0.5 | 0.5 | 0.5 | 0.5 |
| Surface hydrophilicity | 2 | 2 | 2 | 2 | 2 | 2 | 2 | 2 | 2 |
| Surface lubricity | 10 | 10 | 10 | 10 | 9 | 9 | 10 | 10 | 10 |

TABLE 4

| Component | Comparative Example 2-1 Blending amount (w/w %) | Comparative Example 2-2 Blending amount (w/w %) | Comparative Example 2-3 Blending amount (w/w %) | Comparative Example 2-4 Blending amount (w/w %) |
|---|---|---|---|---|
| 2-Hydroxyethyl methacrylate | 29 | 29 | 34 | 19 |
| PEG400 monomethacrylate | 20 | — | — | — |
| N-Vinyl-2-pyrrolidone | — | 10 | — | 10 |
| Methacrylic acid | — | — | 5 | — |
| N,N-Dimethylacrylamide | — | — | — | 10 |
| 3-[Tris(trimethylsiloxy)silyl]propyl methacryloyloxyethyl succinate | 50 | 60 | 60 | — |
| TRIS | — | — | — | 60 |
| Ethylene glycol dimethacrylate | 0.5 | 0.5 | 0.5 | 0.5 |
| Azobisisobutyronitrile | 0.5 | 0.5 | 0.5 | 0.5 |
| Surface hydrophilicity | 0 | 0 | 0 | 0 |
| Surface lubricity | 1 | 2 | 1 | 1 |

INDUSTRIAL APPLICABILITY

The silicone contact lens having surface hydrophilicity and surface lubricity is provided.

The invention claimed is:

1. A branched polyoxyethylene compound, which is represented by the following formula (1):

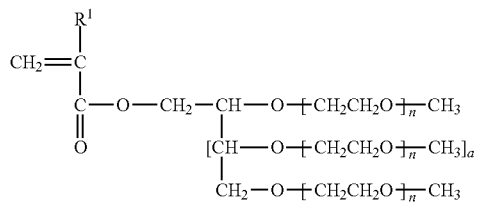

where n represents from 3 to 1,150, a represents 0 or 2, and $R^1$ represents a hydrogen atom or a methyl group.

2. A silicone contact lens, comprising, on a surface thereof, a graft polymer containing a constituent unit represented by the following formula (1'):

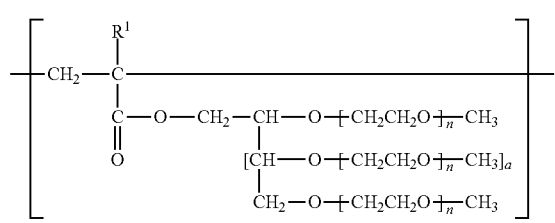

where n represents from 3 to 1,150, a represents 0 or 2, and $R^1$ represents a hydrogen atom or a methyl group.

3. A contact lens, comprising a constituent unit represented by the following formula (1'):

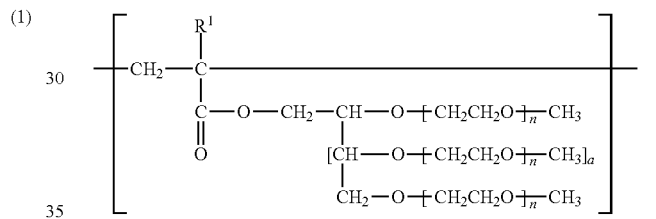

where n represents from 3 to 1,150, a represents 0 or 2, and $R^1$ represents a hydrogen atom or a methyl group.

4. A branched polyoxyethylene compound according to claim 1, wherein the n represents from 3 to 600, the a represents 0 or 2, and the $R^1$ represents a hydrogen atom or a methyl group.

5. A silicone contact lens according to claim 2, wherein the n represents from 3 to 600, the a represents 0 or 2, and the $R^1$ represents a hydrogen atom or a methyl group.

6. A contact lens according to claim 3, wherein the n represents from 3 to 600, the a represents 0 or 2, and the $R^1$ represents a hydrogen atom or a methyl group.

* * * * *